United States Patent
Derrien et al.

(10) Patent No.: US 8,866,891 B2
(45) Date of Patent: Oct. 21, 2014

(54) METHOD FOR THE NON-DESTRUCTIVE INSPECTION OF A MECHANICAL PART

(75) Inventors: Gerard Derrien, Houilles (FR); Claude Leonetti, Courcouronnes (FR)

(73) Assignee: SNECMA, Paris (FR)

( * ) Notice: Subject to any disclaimer, the term of this patent is extended or adjusted under 35 U.S.C. 154(b) by 492 days.

(21) Appl. No.: 13/142,075

(22) PCT Filed: Dec. 21, 2009

(86) PCT No.: PCT/FR2009/001468
§ 371 (c)(1),
(2), (4) Date: Aug. 24, 2011

(87) PCT Pub. No.: WO2010/072920
PCT Pub. Date: Jul. 1, 2010

(65) Prior Publication Data
US 2011/0298901 A1      Dec. 8, 2011

(30) Foreign Application Priority Data

Dec. 24, 2008   (FR) ........................................ 08 07460
Jul. 3, 2009    (FR) ........................................ 09 03289

(51) Int. Cl.
| | | |
|---|---|---|
| H04N 13/02 | (2006.01) | |
| G01N 21/95 | (2006.01) | |
| G05B 19/401 | (2006.01) | |
| G06T 7/00 | (2006.01) | |
| G01N 21/88 | (2006.01) | |
| G01N 21/91 | (2006.01) | |

(52) U.S. Cl.
CPC .... *G01N 21/9515* (2013.01); *G01N 2021/8854* (2013.01); *G05B 2219/37206* (2013.01); *G05B 2219/37205* (2013.01); *G05B 2219/35075* (2013.01); *G01N 2021/9518* (2013.01); *G05B 19/401* (2013.01); *G06T 7/001* (2013.01); *G06T 2207/30164* (2013.01); *G05B 2219/37563* (2013.01); *G01N 21/91* (2013.01); *G01N 2021/8867* (2013.01)
USPC .......................................................... 348/50

(58) Field of Classification Search
CPC .............. G01N 2021/8854; G01N 2021/8867; G01N 2021/9518; G01N 21/91; G01N 21/9515; G05B 2219/35075; G05B 2219/37206; G05B 2219/37563
See application file for complete search history.

(56) References Cited

U.S. PATENT DOCUMENTS

| | | | | |
|---|---|---|---|---|
| 5,175,601 A | * | 12/1992 | Fitts | ............................... 356/604 |
| 5,963,328 A | | 10/1999 | Yoshida et al. | |

(Continued)

FOREIGN PATENT DOCUMENTS

WO   WO 00/63681   10/2000

OTHER PUBLICATIONS

International Search Report issued Mar. 16, 2010, in PCT/FR2009/001468.

(Continued)

*Primary Examiner* — Dave Czekaj
*Assistant Examiner* — M D Haque
(74) *Attorney, Agent, or Firm* — Oblon, Spivak, McClelland, Maier & Neustadt, L.L.P.

(57) ABSTRACT

An automatic method of non-destructive inspection of a mechanical part by comparing images of the surface of the part with reference images recorded in a database, by a digital image acquisition device including an image sensor, a lighting source, and a mechanism for moving the image sensor and the lighting source relative to the mechanical part.

11 Claims, 3 Drawing Sheets

(56) References Cited

U.S. PATENT DOCUMENTS

| | | | |
|---|---|---|---|
| 6,943,876 B2* | 9/2005 | Yoshida et al. | 356/237.2 |
| 7,474,416 B2* | 1/2009 | Lindner et al. | 356/606 |
| 2002/0176010 A1* | 11/2002 | Wallach et al. | 348/229.1 |
| 2003/0133604 A1* | 7/2003 | Neumann | 382/149 |
| 2006/0119864 A1 | 6/2006 | Lindner et al. | |
| 2007/0064998 A1* | 3/2007 | Umeda et al. | 382/149 |
| 2007/0122026 A1* | 5/2007 | Ersue et al. | 382/141 |
| 2007/0196012 A1 | 8/2007 | Lin et al. | |
| 2008/0031510 A1* | 2/2008 | Jung | 382/149 |

OTHER PUBLICATIONS

Von Hans Grabowski, et al., "Qualitätsprüfung von Werkstücken mit bildverarbeitenden Systemen: Neuer Ansatz mit Produktmodelldaten als Basis", VDI-Z, vol. 134, No. 10, XP 000324019, Oct. 1, 1992, pp. 128-132, 135-136, 139.

* cited by examiner

METHOD FOR THE NON-DESTRUCTIVE INSPECTION OF A MECHANICAL PART

BACKGROUND OF THE INVENTION

1. Field of the Invention

The present invention relates to a method of non-destructive inspection of a mechanical part, such as for example a turbomachine component.

2. Description of the Related Art

The wear of certain turbomachine parts can be inspected by a penetrant sweating technique that is effective in detecting compact defects that open to the surface and that are not obstructed, such as cracks, pores, or folds.

That technique requires the use of colored or fluorescent liquids presenting low surface tension and commonly referred to as "penetrants", that are capable of penetrating by capillarity into open defects in parts. After such penetrants have been applied to the parts, have become impregnated, and then excess penetrant remaining on the surface has been eliminated, defects are made to appear by applying a fine layer of powder to the parts, which powder is made up of capillary tubes suitable for sucking up the penetrants that have penetrated into discontinuities of the part.

The sweating technique is nevertheless found to be constraint in practice, in particular since it requires a suitably qualified operator to act in order to interpret the results.

Furthermore, it can be relatively dangerous and polluting in that it makes use of substances that are flammable, volatile, and harmful.

Methods are also known for optically inspecting a mechanical part (e.g. from document US 2007/0122026A1), which methods consist in automatically defining a path for an image sensor and lighting means to move over the surface of the part, the path being established from a survey of the surface of the part or from digital data defining the surface of the part, with movement of the image sensor along said path serving to acquire images of the entire surface of the part. Those images then need to be examined and analyzed in order to detect defects in the surface of the part, with such examination and analysis giving rise to problems that have not been solved in satisfactory manner to date.

BRIEF SUMMARY OF THE INVENTION

A particular object of the invention is to provide a solution to those problems that is inexpensive and effective, making it possible to process the acquired images and optimize them automatically.

A particular object of the invention is to enable mechanical parts to be inspected in a manner that can be implemented simply and quickly and that can be performed automatically and optically, without contact.

To this end, the invention provides an automatic method of non-destructively inspecting a mechanical part by means of a device comprising an image sensor, a lighting source, and means for moving the image sensor, the lighting source, and the mechanical part relative to one another, the method consisting essentially in making a three-dimensional survey of the surface of the part, defining a subdivision of the surface of the part into zones suitable for being photographed by the image sensor, defining respective paths for the image sensor and for the lighting source relative to the part, and acquiring images of said zones of the surface of the part, the method being characterized in that it also consists in:

analyzing the images and determining zones in the images that are over-exposed or under-exposed;

optimizing optical parameters for image acquisition of said zones and defining a second subdivision of the surface of the part, taking account of the optimization of said optical parameters for said zones;

defining a new path for the image sensor and a new path for the lighting source that enable images to be acquired of the surface of the part while using the optimized optical parameters and the second subdivision;

acquiring images of said zones while following the new paths and recording the images; and automatically determining any surface defects of the part in the recorded images and comparing them with known defects recorded in a database.

The non-destructive inspection method proposed by the invention presents good sensitivity to surface defects in parts, and it enables the time required for preparing parts for inspection to be reduced considerably.

This method is also found to be less expensive in that it does not require any consumable to be used, and the method can be implemented by relatively unqualified personnel.

The method of the invention also makes it possible to avoid dangers associated with using substances that are flammable, volatile, and harmful, and the drawbacks that result therefrom that are inherent to managing liquid waste.

Prior to any use, each part may be previously subjected to a three-dimensional survey of the topology of its surface, so as to guarantee the accuracy of subsequent non-destructive inspections by enabling the image sensor and the lighting source to be accurately located facing the surface of the part and regardless of any observed differences in the position or the shape thereof. In this way, with the method of the invention, it is possible to analyze any type of part going from a new part (prior to any use) to a part that has been used or that is worn. The three-dimensional survey also makes it possible to track variation in the state of the part over time. This is advantageous when there is a likelihood of significant differences of shape existing between different parts of the same type.

The three-dimensional survey of the surface and the definition of the image acquisition program may be performed on a single occasion for a given type of mechanical part, thus enabling time to be saved without significantly reducing the accuracy of inspections, providing the differences in shape and appearance that are likely to exist between different parts of the same mass-produced part are negligible, i.e. providing that shape defects are smaller than the accuracy with which the optical sensor and the lighting source are located and that their differences of appearance lie within a defined range of settings in the database.

According to another characteristic of the invention, the method also consists in previously building up a database in which reference images are recorded of mechanical part surfaces that present typical defects, each image being recorded together with data about surface characteristics, such as the nature of the material and its roughness, with information relating to lighting and picture-taking conditions, and with an indicator of the quality with which a defect is detected in the surface of the part, the method subsequently consisting in recording in said database modifications to the optical parameters and the acquisition paths and the results of inspections performed on the various parts.

This database is initially built up using as great a quantity of information as possible, which information may be collected on a part for inspection and on standard parts or pieces that present known typical defects, of characteristics that have been measured using known non-destructive inspection methods, after which the database is enlarged to or "nourished" with the results of inspections performed on the various parts that are examined in succession. Once the database is well "nourished", the execution of the method of the invention can be simplified, e.g. in terms of optimizing images, as explained below.

According to another characteristic of the invention, the method also consists, after taking a three-dimensional survey of the surface of the part, in generating a digital model of said surface in the form of mathematical curves such as Bezier curves and non-uniform rational basis splines (NURBS) functions, and in repositioning the image sensor and the lighting source relative to the parts by using the three-dimensional survey.

According to another characteristic of the invention, the optical parameters for acquiring images are optimized by varying the intensity and the angle of incidence of the lighting produced by the lighting source, and in determining the optimum value for the intensity and the angle of incidence of the lighting by comparing images with one another with reference to the database while establishing a relationship between the level of surface defect detection and both the surface characteristics and also the intensity and the angle of incidence of the lighting.

This optimization also consists in verifying that the surface area of each zone resulting from the secondary subdivision is smaller than the field covered by the image sensor, and that the standard deviation of the normals at all points of said zones is less than a predetermined minimum value.

The optimization applies to determined zones in the images of a primary subdivision that are representative of real conditions of over-exposure, of under-exposure, or of proper exposure to the lighting, while acquiring images in real time under the measurement conditions.

This makes it possible to define optimum values for the intensity and the angle of lighting by comparing images with one another in each characteristic zone with reference to the above-mentioned database so as to establish a relationship between the level with which surface defects are detected, and both the surface characteristics and also the intensity and the angle of incidence of the lighting delivered by the lighting source, and then to determine the optimum lighting and sensor position parameters for each image to be taken of a secondary subdivision.

Finally, respective paths are determined for the lighting source and for the sensor that enable the images to be acquired of the secondary subdivision while using the optimized parameters.

Optimizing images by discrete re-subdivision of the zones in question and by adjusting optical parameters for image acquisition and/or by verifying the standard deviation of the normals at all points of the zones may be repeated as often as necessary in order to obtain a result of quality that is sufficient.

Repeated optimization and recording of results in the database serves to "nourish" it, so that subsequently, where necessary, on parts for inspection later on, it is possible to use only one of the above-mentioned optimization methods involving setting acquisition optical parameters or verifying the standard deviation of the normals.

In an embodiment of the invention, the method consists in moving the image sensor and the lighting source relative to the mechanical part by means of a robot arm having one end carrying the image sensor and by means of a steerable device for supporting the lighting source.

The robot arm enables the image sensor and the lighting source to be moved around the mechanical part in order to acquire successive images of the entire surface area of the part under optimum conditions of surface lighting and of focal length adjustment.

The image sensor may be carried by a first robot arm serving to point the image sensor substantially along the normal to the surface under consideration, with the lighting source being carried by a second robot arm, synchronously with the first arm, thus enabling the angular orientation of the lighting source to be modified relative to the part independently of the movement of the sensor.

In certain image acquisition configurations, the orientation of the lighting source is such that the angle of incidence of the light rays is grazing relative to the surface under consideration of the part.

The subdivision of the surface of the part is advantageously defined in such a manner that the image of each zone presents a predetermined amount of overlap with the images of the neighboring zones.

This makes it possible to guarantee that no portion of the surface of the part escapes inspection.

According to another characteristic of the invention, the image sensor is a camera having a matrix of photodetectors of the charge coupled device (CCD) or complementary metal oxide semi-conductor (CMOS) type.

Such a camera enables images to be acquired that present good resolution and that are in digital format, while also being relatively inexpensive.

BRIEF DESCRIPTION OF THE SEVERAL VIEWS OF THE DRAWINGS

The invention can be better understood and other details, advantages, and characteristics thereof appear more clearly on reading the following description made by way of non-limiting example and with reference to the accompanying drawings, in which.

DETAILED DESCRIPTION OF THE INVENTION

Figure 1:
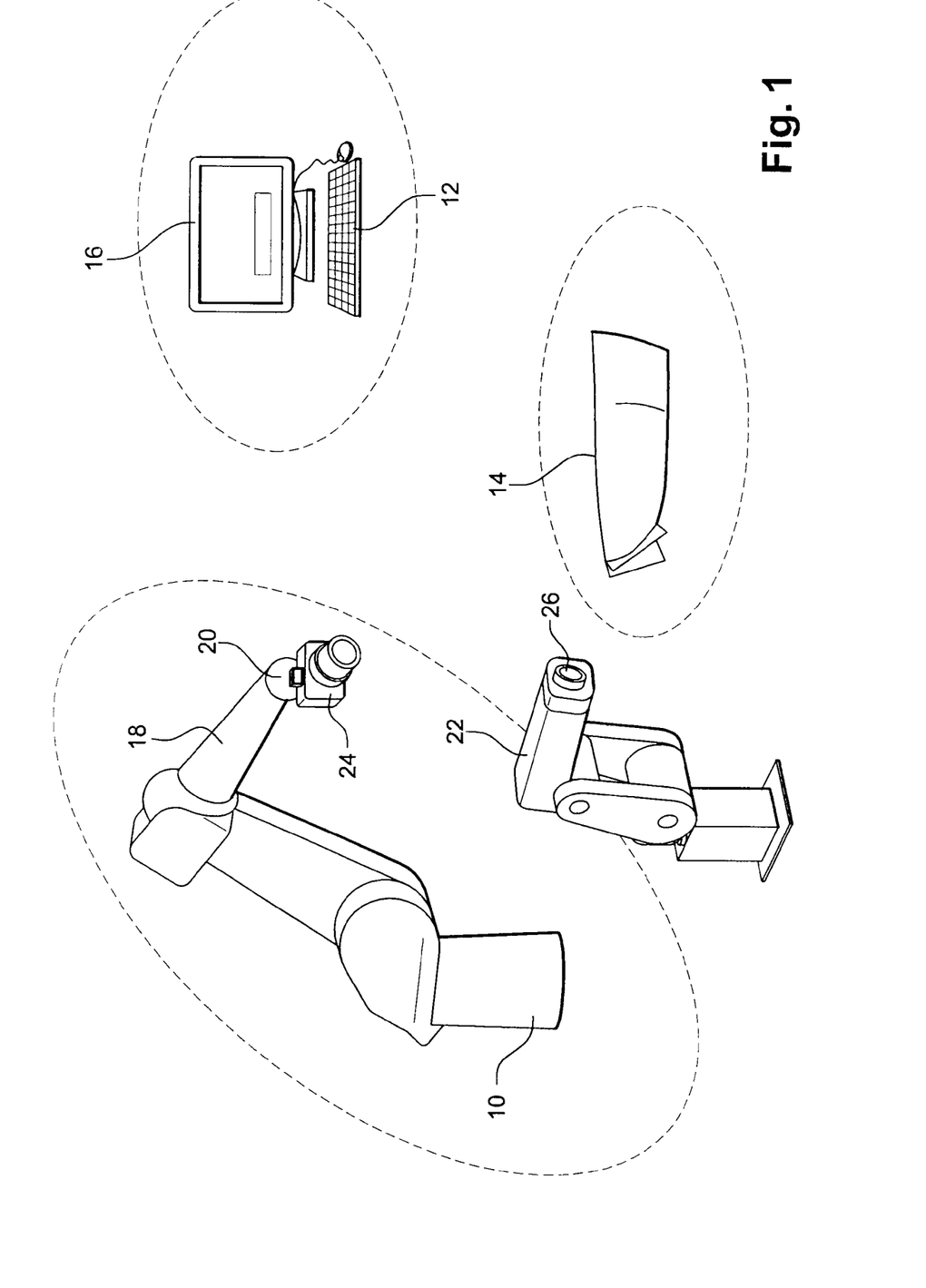
FIG. 1 is a diagrammatic view of the means implemented in the method of the invention.

FIG. 1 is a diagram showing means 10, 12 for implementing the method of non-destructively inspecting mechanical parts as proposed in the context of the invention, together with a part 14 for inspection, such as for example a turbomachine fan blade 14.

The means implemented in the non-destructive inspection method comprise a digital image acquisition device 10 coupled to a lighting device and to image processor means 12, e.g. comprising a microcomputer 16 of PC or analogous type, which is preferably capable of controlling the image acquisition device 10 and the lighting device.

The digital image acquisition device 10 comprises at least one robot arm 18 having one end 20 including hinged means for supporting an image sensor 24. The lighting device includes hinge means 22 for supporting a lighting source 26.

By way of example, the image sensor 24 is a camera having an array of photodetectors of the CCD or the CMOS type, commonly referred to as a "digital camera".

The image processor means 12 are connected to or include a database having reference images recorded therein of the surfaces of mechanical parts of various types presenting typical defects (cracks, scratches, impacts, . . . ), each image being recorded together with data relating to certain surface characteristics, such as the nature of the material and its roughness, together with information relating to lighting and picture-taking conditions, and together with an indicator concerning the quality with which a defect present on the surface of the part is detected. A reference image of a real defect or of an optical artifact is constituted in particular by a substantially uniform gray background and by a portion having a gray level that is higher or lower than that of the uniform background. The substantially uniform gray background is defined as having a determined gray level value, to within a tolerance value.

The reference image database is prepared prior to implementing the method. Optical means are used for acquiring images of parts that include known defects. These images are validated by being compared with one or more reference methods that are commonly used in non-destructive inspection, such as, for example: thermal imaging or eddy currents. Those methods are implemented using instruments that can be moved by the robot arm. The parts used for establishing the database may be different from the parts that are to be inspected.

For each image, the reference image database comprises information relating to:
- the gray level of the image background;
- the material on which the image was taken;
- the method of fabricating the part, such as for example milling, casting, . . . ;
- the surface state of the part (roughness, . . . );
- the measurement conditions used for taking the image, and including in particular data about the lighting, the focal length, the lens aperture, and the exposure time;
- the type and the shape of the defect in the event that the image indicates that a defect is present;
- the presence of an optical artifact;
- the stress field present in the portion of the part being photographed; and
- the number $\underline{n}$ of times that an image of a given zone has been acquired by the method of the invention.

The above-mentioned database may be hosted on a dedicated computer server connected to the microcomputer 16 by a computer network, or it may be hosted directly on the microcomputer 16.

Figure 2:
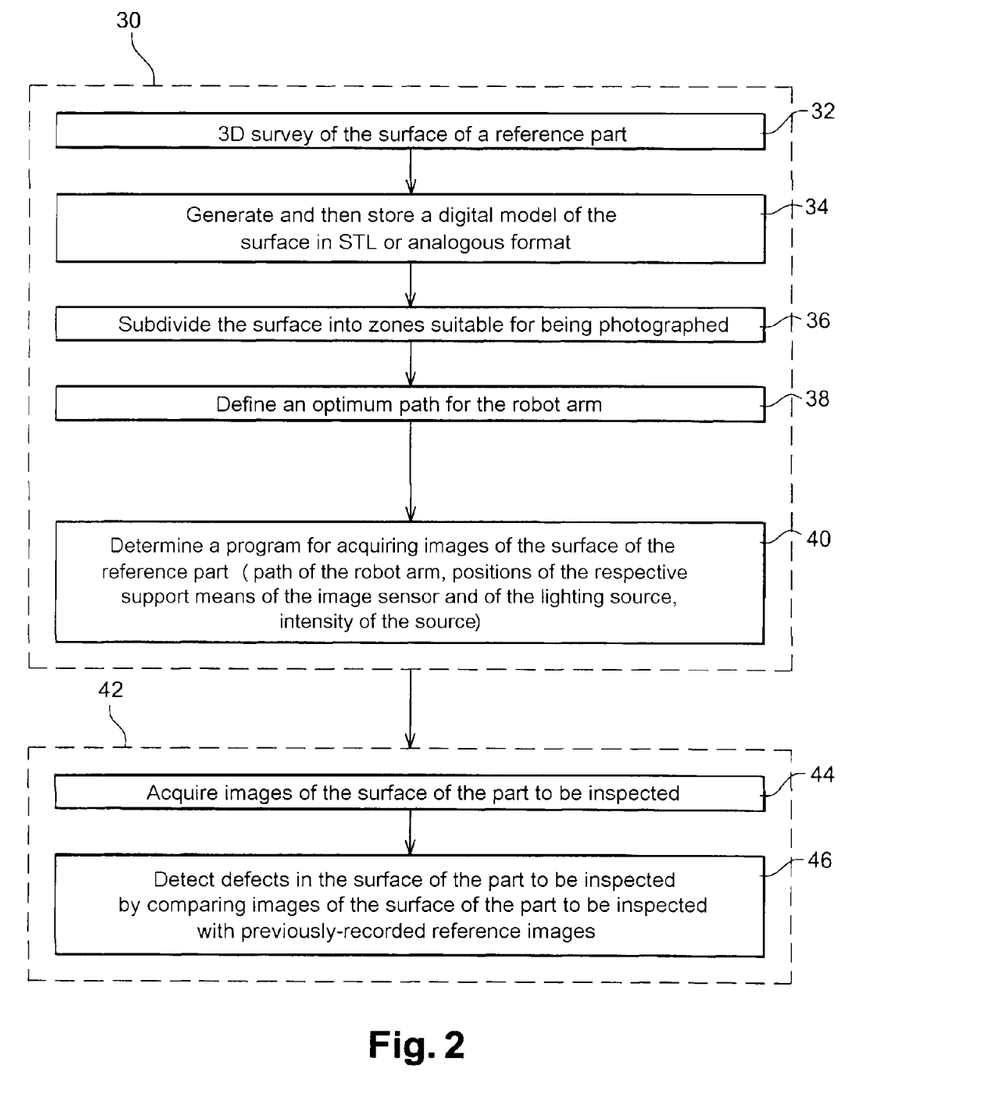
FIG. 2 shows the main steps of the method of the invention.

FIG. 2 shows the main successive stages of the non-destructive inspection method of the invention.

The method comprises a first stage 30 of defining a program for acquiring images of the surface of a part.

In a first step 32, a three-dimensional (3D) survey is taken of the surface of the part that is to be inspected using conventional 3D measurement means, e.g. of the contactless type, and then a digital model of the surface is generated in STL format in a step 34 on the basis of the three-dimensional survey. A simplified model of the three-dimensional survey is made in the form of 3D mathematical surfaces made up of Bezier curves and NURBS, in a neutral digital format of the IGES type that is compatible with standard systems of computer-assisted design and manufacture.

A step of repositioning the optical sensor and the lighting source is performed in order to position them correctly relative to the part by using the three-dimensional survey.

This repositioning step consists essentially in using a known theoretical digital model for positioning the lighting source and the optical sensor for a part of a given type and in correcting those theoretical positions for the lighting source and the optical sensor by using geometrical information derived from the three-dimensional survey. For a given type of part, e.g. a blade, a three-dimensional model is established for positioning the optical sensor and the lighting source that makes it possible theoretically to acquire images of the entire part. Nevertheless, differences in shape between the real part and a theoretical part, and also differences due to the real positioning of the image acquisition device 10 and of the lighting require repositioning that is conventionally performed manually by an operator who corrects each position of the optical sensor and of the lighting source for each acquisition position in order to guarantee correct optical acquisition. Incorporating a prior step of three-dimensionally measuring the part in the method makes it possible to perform this repositioning step automatically.

In practice, the prior three-dimensional measurement makes it possible to calculate real normals in each acquisition position, which normals are used for adjusting the real positions of the optical sensor and of the lighting source relative to the part.

This step thus makes it possible to reposition an acquisition device accurately and automatically relative to the real part.

The following step 36 of the method consists initially in defining zones that are suitable for being photographed. To do this, the surface of the part for inspection is subdivided into primary zones that are suitable for being photographed by the image sensor 24. Image acquisition is performed by positioning the sensor and the lighting source while using parameters contained in the reference image database, i.e. parameters relating to the material of the surface being photographed, to its roughness, and to its shape.

The program for subdividing the surface of the part into primary zones is defined either on the part being studied, or else on a reference part. In this prior step, the operator defines picture-taking parameters so that the pictures that are taken have a gray level that is as uniform as possible. The parameters (sensor position, picture-taking parameters, . . . ) may be organized in a database specifically associated with the part being studied. Thus, the operator may load the parameters required for executing this first subdivision step by calling the reference of the part.

This first step of subdividing the part serves to verify that the appearance of the part being studied is uniform relative to reference settings in the database. For example, certain parts require additional machining at the end of a production cycle in order to remove any machining swarf or in order to provide dynamic balancing. The frequency of such additional machining and also the locations thereof on any given part are random. The overall appearance of one particular type of part thus varies from one part to another, certain parts randomly presenting zones that are brighter than others. The use of a pre-established program makes it possible to detect these zones and to process them specifically.

At the end of this first step of analyzing the image of the primary subdivision, zones of these images presenting a non-uniform appearance are detected, i.e. zones presenting over-exposure or under-exposure relative to the setting obtained from the database. For this purpose, each non-uniform zone is segmented into a plurality of portions and a plurality of digital images are acquired of these portions while varying the incidence and the intensity of the lighting, the settings and the orientation of the focal length, and also the exposure time of the sensor, these acquisition parameters being determined while taking account of the material of the part, of the fabrication method thereof, and also of its surface state.

After optimizing two-dimensional (2D) acquisition settings over all of the over- or under-exposed zones, a new subdivision is made that is optimized for all of the zones.

This new subdivision process essentially consists in defining zones of the part, and in verifying firstly that the dimensions of each zone are less than or equal to the linear field covered by the image sensor, and secondly that the standard deviation angle for the set of normals in the zone under consideration is less than a predetermined value that depends on the desired level with which surface defects are to be detected on the part and on the depth of field of the image sensor.

This predetermined value is obtained by coupling together a plurality of parameters. For this purpose, the 3D curvature may be measured in each zone and combined with the depth of field of the optical sensor, thereby obtaining information about the level of detection that will be obtained. In order to ensure that defects are detected, a maximum value is defined for the angle difference between the normal to the focal plane and the normal to a point of a defect, with this being done by using the reference image database. It is thus necessary for the standard deviation angle for the set of normals in each zone to be less than the maximum detection angle value of the focal plane under consideration.

The maximum value for the difference angle is defined experimentally using standard parts. To do this, a standard part is placed facing the sensor and the difference angle is determined beyond which it is not possible to obtain a satisfactory image.

The subdivision process is preferably designed so that the image of each zone presents a certain amount of overlap with the images of neighboring zones, so as to guarantee that the entire surface of the part is covered by the image sensor during the image acquisition program.

The following step 38 consists in defining an optimum path to be followed by the robot arm 18 so as to bring the image sensor 34 successively onto the mean normal of each predetermined secondary zone of the surface of the part, at the distance D from said surface, while also minimizing the number of movements of the robot arm.

By extrapolating the results of optimizing the settings to all of the secondary zones, it is possible in a step 40 to determine a complete program for acquiring images of the surface of the part, the program comprising a path for the robot arm, for the means 20 for supporting the image sensor, and for the means 22 for supporting the lighting source, thus enabling the image sensor 24 and the lighting source 26 to be brought in succession into their respective optimum positions for acquiring an image of each zone of the surface of the part, and also to determine the optimum variation in the intensity of illumination by the lighting source along this path.

Non-destructive inspection is performed during a second stage 42, with the surface of the part for inspection being subdivided into secondary optical acquisition zones as optimized during the above-described stage 30. An image of each zone of the surface of the part to be inspected is recorded in a step 44 while following the image acquisition program as obtained from the three-dimensional survey of the topology of the surface of the part.

Image processing algorithms are applied in a step 46 to the images of each of the zones. These algorithms consist essentially in extracting from an image of a zone those portions that correspond to non-uniformities in the gray level relative to the remainder of the image. These portions are subsequently compared with images from the reference database that have the same geometrical shape and the same surface characteristics, i.e. surface roughness that is identical, material that is identical to that from which the image was obtained, and an identical method of obtaining the surface. For each image under study, a comparison is made for example between the spatial distribution of the gray levels of the non-uniform portions surveyed on the zone being studied, with the defects present on the images in the reference image database.

The comparison gives rise to two results:
either no match is made with an image of the reference image database;
or else a match is made.

For the first result, where no match is made with the reference image database for an image of a given zone of the part, then the zone is analyzed by means of a conventional non-destructive inspection instrument carried by the robot arm in order to determine whether or not a defect is present. This information is then recorded in the reference image database together with the image and in association in particular with the conditions under which the image was acquired, the surface state, and the type of material of the part.

With the second result, when a match is made with an image in the reference image database, then a reliability criterion is applied to the match, and consists in searching the reference image database for the number $\underline{n}$ of times that such an image has already been photographed. If $\underline{n}$ is greater than a predetermined threshold value N, then the detection is considered as being reliable and the image is associated with information relating to the presence or the absence of a defect. If $\underline{n}$ is less than the threshold value N, then a non-destructive inspection method with a conventional instrument is implemented so as to confirm the information about the presence or absence of a defect. The number of times such a match is made with an image in the reference image database is then incremented to n+1.

The method of the invention can thus be implemented without human intervention, providing there exists a reliable match with the reference image database. When it is necessary to use conventional non-destructive inspection means, then the image that has been obtained is incorporated in the reference image database in order to enlarge the database and improve future detection.

The above-described non-destructive inspection method makes it possible to detect defects with sensitivity that is comparable to penetrant sweating techniques, while presenting numerous advantages compared with those techniques, as mentioned above.

This method presents in particular the advantage of being suitable for being entirely automated. The method is also self-adaptive. Whatever the initial position of the part relative to the lighting source and relative to the sensor, and whatever the shape of the part, it is possible by means of the initial three-dimensional acquisition to perform a non-destructive inspection operation.

Figure 3:
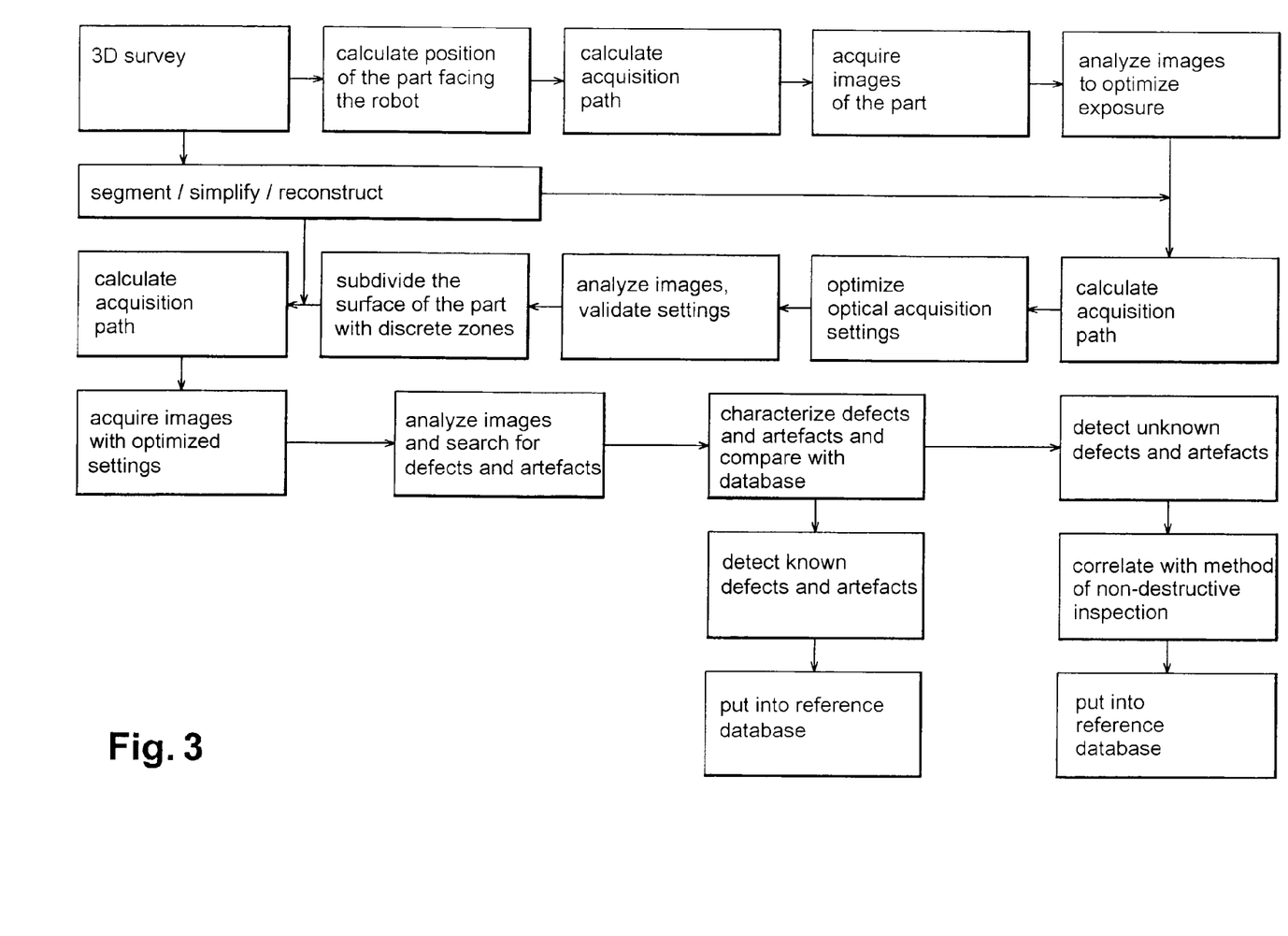
FIG. 3 is a flow chart of the method of the invention.

FIG. 3 is a diagrammatic flow chart of the method of the invention, essentially comprising:
making a three-dimensional survey of the surface of the part, on the basis of which the real position of the part is calculated relative to the lighting device and the picture-taking device;
calculating a path for the device for optically acquiring two-dimensional images of the surface of the part;
acquiring overall images of the part by using parameters from the database relating to the material, the roughness, and the surface shape of the part;
analyzing the images and determining zones in the images that serve to optimize optical settings associated with the exposure as a function of parameters that appear in the database about the orientation of the picture-taking sensor, the lighting, and the surface shape;
calculating a path for acquiring images, which path serves to optimize the optical settings, while taking account of the above analysis and of a path for the lighting device;
optimizing optical settings for acquiring images of the above-defined zones;

analyzing images, validating optimized settings for the various zones and storing them in the database;

subdividing the surface of the part into discrete acquisition zones that take account of the optimized settings so as to obtain a best quality image from each discrete zone (this process serving to subdivide a zone that presents an image defect, e.g. local over-exposure, into zones that are smaller and more uniform and for which lighting and image-taking parameters are adjusted to optimum values);

thereafter, in combination with the result of a step of segmenting, simplifying, and reconstructing, calculating a real-time image-acquisition path;

taking images of the surface of the part with the optimized settings;

analyzing the images and searching for defects and optical artifacts;

characterizing the defects and artifacts that are found and comparing them with known defects and artifacts stored in a database, on the basis of their weight in pixels, of the 3D curvature of the part, and of the distribution of each defect in a longitudinal direction and in a transverse direction;

thereafter, if the defects and artifacts that have been found are already known, recording them in the reference database and issuing a corresponding report;

or else, if the defects and artifacts that are found do not appear in the database, correlating them by applying non-destructive inspection methods (e.g. using eddy currents or thermal imaging) identifying them as being new defects or new artifacts, and recording them in the reference database.

The invention claimed is:

1. An automatic method of non-destructively inspecting a mechanical part by a device including an image sensor, a lighting source, and a mechanism which moves the image sensor, the lighting source, and the mechanical part relative to one another, the method comprising: making, using a computer, a three-dimensional survey of a surface of the part; defining, using the computer, a first subdivision of the surface of the part into zones suitable for being photographed by the image sensor; defining, using the computer, respective paths for the image sensor and for the lighting source relative to the part; acquiring images of the zones of the surface of the part; analyzing, using the computer, the images and determining, using the computer, zones in the images that are over-exposed or under-exposed; optimizing, using the computer, optical parameters for image acquisition of the zones in the images that are over-exposed or under-exposed and defining, using the computer, a second subdivision of the surface of the part based on optimization of the optical parameters for the zones in the images that are over-exposed or under-exposed; defining, using the computer, a new path for the image sensor and a new path for the lighting source that enable images to be acquired of the surface of the part based on the optimized optical parameters and the second subdivision; acquiring images of the zones while following the new paths and recording the images; comparing, using the computer, the recorded images with reference images recorded in a database; and automatically determining, using the computer, any surface defects of the part in the recorded images based on the comparing the recorded images with the reference images recorded in the database, wherein when the recorded images do not match the reference images recorded in the database, a non-destructive inspection of the surface of the part is performed using a nondestructive inspection instrument carried by the mechanism to determine whether a defect is present, and the database is updated to include the recorded images and the results of the nondestructive inspection, and wherein the optimizing further includes verifying, using the computer, that the surface area of each zone resulting from the secondary subdivision is smaller than a field covered by the image sensor, and standard deviation of the normals at all points of the zones is less than a predetermined minimum value.

2. A method according to claim 1, further comprising previously building up a database in which reference images are recorded of mechanical part surfaces that present typical defects, each image being recorded together with data about surface characteristics, or a nature of the material and its roughness, with information relating to lighting and picture-taking conditions, and with an indicator of the quality with which a defect is detected in the surface of the part, the method subsequently recording in the database modifications to the optical parameters and the acquisition paths and the results of inspections performed on the various parts.

3. A method according to claim 1, wherein the three-dimensional survey of the surface of the part is performed once only for any given type of mechanical part, providing the differences in shape and appearance between the parts being inspected are small or substantially zero.

4. A method according to claim 1, wherein the part for inspection is subjected to a three-dimensional survey of its surface whenever the part for inspection presents non-negligible differences of shape and appearance compared with other inspected parts.

5. A method according to claim 1, further comprising, after taking a three-dimensional survey of the surface of the part, generating, using the computer, a digital model of the surface in a form of mathematical curves or Bezier curves and NURBS functions, and repositioning the image sensor and the lighting source relative to the parts by using the three-dimensional survey.

6. A method according to claim 1, wherein the optical parameters for acquiring images are optimized by varying an intensity and angle of incidence of the lighting produced by the lighting source, and further comprising determining, using the computer, the optimum value for the intensity and the angle of incidence of the lighting by comparing images with one another with reference to the database while establishing a relationship between the level of surface defect detection and both the surface characteristics and the intensity and the angle of incidence of the lighting.

7. A method according to claim 1, further comprising moving the image sensor and the lighting source relative to the mechanical part by robot arms respectively carrying the image sensor and the lighting source.

8. A method according to claim 1, wherein the image sensor is a camera having a matrix of photodetectors of the CCD or CMOS type.

9. A method according to claim 1, further comprising: making, using the computer, a three-dimensional survey of the surface of the part, on the basis of which the real position of the part is calculated relative to the lighting device and the picture-taking device; calculating, using the computer, a path for the device for optically acquiring two-dimensional images of the surface of the part; acquiring, using the computer, overall images of the part by using parameters from the database relating to the material, the roughness, and the surface shape of the part; analyzing, using the computer, the images and determining, using the computer, zones in the images that serve to optimize optical settings associated with the exposure as a function of parameters that appear in the database about the orientation of the picture-taking sensor, the lighting, and the surface shape; calculating, using the computer, a path for acquiring images, which path serves to optimize the optical settings, while taking account of the above analysis and of a path for the lighting device; optimizing, using the computer, optical settings for acquiring images of the defined zones; analyzing images, validating optimized settings for the various zones and storing the optimized settings in the database; subdividing, using the computer, the surface of the part into discrete acquisition zones that take account of the optimized settings; thereafter, in combination with the result of a segmenting, simplifying, and reconstructing, calculating, using the computer, a real-time image-acquisition path; taking images of the surface of the part with the optimized settings; analyzing, using the computer, the images and searching for defects and optical artifacts; and characterizing, using the computer, the defects and artifacts that are found and comparing the found defects and artifacts with known defects and artifacts stored in a database.

10. A method according to claim 6, wherein the optimum value for the intensity and the angle of incidence of the lighting is determined, using the computer, based on an angle difference between a normal to a focal plane and a normal to a point of a defect using known defects in the database.

11. An automatic method of non-destructively inspecting a mechanical part by a device including an image sensor, a lighting source, and a mechanism which moves the image sensor, the lighting source, and the mechanical part relative to one another, the method comprising: making, using a computer, a three-dimensional survey of a surface of the part; defining, using the computer, a first subdivision of the surface of the part into zones suitable for being photographed by the image sensor; defining, using the computer, respective paths for the image sensor and for the lighting source relative to the part; acquiring images of the zones of the surface of the part; analyzing, using the computer, the images and determining, using the computer, zones in the images that are over-exposed or under-exposed; optimizing, using the computer, optical parameters for image acquisition of the zones in the images that are over-exposed or under-exposed and defining, using the computer, a second subdivision of the surface of the part based on optimization of the optical parameters for the zones in the images that are over-exposed or under-exposed; defining, using the computer, a new path for the image sensor and a new path for the lighting source that enable images to be acquired of the surface of the part based on the optimized optical parameters and the second subdivision; acquiring images of the zones while following the new paths and recording the images; and automatically determining, using the computer, any surface defects of the part in the recorded images and comparing, using the computer, the recorded images with known defects recorded in a database; and, wherein the optimizing further includes verifying, using the computer, that the surface area of each zone resulting from the secondary subdivision is smaller than a field covered by the image sensor, and standard deviation of the normals at all points of the zones is less than a predetermined minimum value.

* * * * *